(12) United States Patent
Cumming

(10) Patent No.: US 9,283,070 B2
(45) Date of Patent: Mar. 15, 2016

(54) VITREOUS COMPRESSING PLATE HAPTIC

(76) Inventor: James Stuart Cumming, Laguna Beach, CA (US)

(*) Notice: Subject to any disclaimer, the term of this patent is extended or adjusted under 35 U.S.C. 154(b) by 88 days.

(21) Appl. No.: 13/092,359

(22) Filed: Apr. 22, 2011

(65) Prior Publication Data

US 2011/0313524 A1 Dec. 22, 2011

Related U.S. Application Data

(60) Provisional application No. 61/398,107, filed on Jun. 21, 2010, provisional application No. 61/398,098, filed on Jun. 21, 2010, provisional application No. 61/398,115, filed on Jun. 21, 2010, provisional application No. 61/398,099, filed on Jun. 21, 2010.

(51) Int. Cl.
*A61F 2/16* (2006.01)

(52) U.S. Cl.
CPC .............. *A61F 2/1624* (2013.01); *A61F 2/1629* (2013.01); *A61F 2002/169* (2015.04); *A61F 2002/1682* (2015.04); *A61F 2002/1689* (2013.01)

(58) Field of Classification Search
CPC ........... A61F 2002/1689; A61F 2/1629; A61F 2/1648; A61F 2/1635; A61F 2/16; A61F 2/169; A61F 2002/169
USPC .................... 623/6.13, 6.18–6.22, 6.37–6.41, 623/6.43–6.5
See application file for complete search history.

(56) References Cited

U.S. PATENT DOCUMENTS

| | | | |
|---|---|---|---|
| 2,834,023 A | 5/1958 | Wolfgang | |
| 4,073,014 A | 2/1978 | Poler | |
| 4,118,808 A | 10/1978 | Poler | |
| 4,122,556 A | 10/1978 | Poler | |
| 4,159,546 A | 7/1979 | Shearing | |
| 4,168,547 A | 9/1979 | Konstantinov et al. | |
| 4,173,798 A | 11/1979 | Welsh | |
| 4,174,543 A | 11/1979 | Kelman | |
| 4,206,518 A | 6/1980 | Jardon et al. | |
| 4,244,060 A | 1/1981 | Hoffer | |
| 4,254,509 A * | 3/1981 | Tennant | 623/6.37 |
| 4,277,851 A | 7/1981 | Choyce et al. | |

(Continued)

FOREIGN PATENT DOCUMENTS

| | | |
|---|---|---|
| CA | 2110184 A1 | 12/1992 |
| CH | 681687 | 5/1993 |

(Continued)

OTHER PUBLICATIONS

Final Office Action for U.S. Appl. No. 13/017,189 dated Jul. 18, 2014 in 10 pages.

(Continued)

*Primary Examiner* — Paul Prebilic
(74) *Attorney, Agent, or Firm* — Knobbe Martens Olson & Bear LLP

(57) ABSTRACT

A plate haptic is used with an intraocular lens. The plate haptic comprises: a plurality of opposing lateral portions; a distal portion having a plurality of opposing projections extending substantially laterally therefrom; and a proximal portion comprising a strap across which is a hinge connecting the lens optic to the haptic. The intersection of the proximal portion with each lateral portion forms a plurality of appendages, or paddles, to partially surround the optic.

18 Claims, 2 Drawing Sheets

(56) References Cited

U.S. PATENT DOCUMENTS

| | | | |
|---|---|---|---|
| 4,298,995 A | 11/1981 | Poler | |
| 4,304,012 A | 12/1981 | Richard | |
| 4,409,690 A | 10/1983 | Gess | |
| 4,409,691 A | 10/1983 | Levy | |
| 4,424,597 A | 1/1984 | Schlegel | |
| 4,441,217 A | 4/1984 | Cozean, Jr. | |
| 4,477,931 A | 10/1984 | Kelman | |
| 4,573,998 A | 3/1986 | Mazzocco | |
| 4,585,457 A | 4/1986 | Kalb | |
| 4,605,411 A | 8/1986 | Fedorov et al. | |
| 4,629,462 A | 12/1986 | Feaster | |
| 4,648,878 A | 3/1987 | Kelman | |
| 4,664,665 A | 5/1987 | Reuss et al. | |
| 4,664,666 A | 5/1987 | Barrett | |
| 4,673,406 A | 6/1987 | Schlegel | |
| 4,681,102 A | 7/1987 | Bartell | |
| 4,704,123 A | 11/1987 | Smith | |
| 4,710,195 A | 12/1987 | Glovinazzo | |
| 4,718,904 A | 1/1988 | Thornton | |
| 4,737,322 A | 4/1988 | Bruns et al. | |
| 4,738,680 A | 4/1988 | Herman | |
| 4,743,254 A | 5/1988 | Davenport | |
| 4,753,655 A | 6/1988 | Hecht | |
| 4,759,761 A | 7/1988 | Portnoy | |
| 4,763,650 A | 8/1988 | Hauser | |
| 4,765,329 A | 8/1988 | Cumming et al. | |
| 4,769,033 A | 9/1988 | Nordan | |
| 4,769,035 A | 9/1988 | Kelman | |
| 4,772,283 A | 9/1988 | White | |
| 4,778,463 A | 10/1988 | Hetland | |
| 4,781,719 A | 11/1988 | Kelman | |
| 4,790,847 A | 12/1988 | Woods | |
| 4,793,344 A | 12/1988 | Cumming et al. | |
| 4,813,955 A | 3/1989 | Achatz et al. | |
| 4,816,030 A | 3/1989 | Robinson | |
| 4,840,627 A | 6/1989 | Blumenthal | |
| 4,842,599 A | 6/1989 | Bronstein | |
| 4,842,601 A | 6/1989 | Smith | |
| 4,846,833 A | 7/1989 | Cumming | |
| 4,862,885 A | 9/1989 | Cumming | |
| 4,865,601 A | 9/1989 | Caldwell et al. | |
| 4,868,251 A | 9/1989 | Reich et al. | |
| 4,880,427 A | 11/1989 | Anis | |
| 4,888,012 A | 12/1989 | Horn et al. | |
| 4,892,543 A | 1/1990 | Turley | |
| 4,919,130 A | 4/1990 | Stoy et al. | |
| 4,932,966 A | 6/1990 | Christie et al. | |
| 4,932,968 A | 6/1990 | Caldwell et al. | |
| 4,932,970 A | 6/1990 | Portney | |
| 4,936,850 A | 6/1990 | Barrett | |
| 4,963,148 A | 10/1990 | Sulc et al. | |
| 4,969,897 A | 11/1990 | Kalb | |
| 4,976,716 A | 12/1990 | Cumming | |
| 4,978,354 A | 12/1990 | Van Gent | |
| 4,994,082 A | 2/1991 | Richards et al. | |
| 5,047,051 A | 9/1991 | Cumming | |
| 5,066,297 A | 11/1991 | Cumming | |
| 5,078,742 A * | 1/1992 | Dahan | 623/6.44 |
| 5,089,022 A | 2/1992 | Koester et al. | |
| 5,139,518 A | 8/1992 | White | |
| 5,141,507 A | 8/1992 | Paraekh | |
| 5,152,788 A | 10/1992 | Isaacson et al. | |
| 5,152,789 A | 10/1992 | Willis | |
| 5,171,319 A | 12/1992 | Keates et al. | |
| 5,171,320 A | 12/1992 | Nishi | |
| 5,180,390 A | 1/1993 | Drews | |
| 5,217,490 A | 6/1993 | Sayano et al. | |
| 5,275,604 A | 1/1994 | Rheinish et al. | |
| 5,275,623 A | 1/1994 | Sarfarazi | |
| 5,275,624 A | 1/1994 | Hara et al. | |
| 5,290,310 A | 3/1994 | Makower et al. | |
| 5,304,182 A | 4/1994 | Rheinish et al. | |
| 5,324,306 A | 6/1994 | Makower et al. | |
| 5,326,347 A | 7/1994 | Cumming | |
| 5,366,502 A | 11/1994 | Patel | |
| 5,376,115 A | 12/1994 | Jansen | |
| 5,425,734 A | 6/1995 | Blake | |
| 5,443,506 A | 8/1995 | Garabet | |
| 5,474,562 A | 12/1995 | Orchowski et al. | |
| 5,476,514 A * | 12/1995 | Cumming | 623/6.37 |
| 5,489,302 A | 2/1996 | Skottun | |
| 5,496,366 A | 3/1996 | Cumming | |
| 5,522,891 A | 6/1996 | Klaas | |
| 5,562,731 A | 10/1996 | Cumming | |
| 5,578,042 A | 11/1996 | Cumming | |
| 5,578,078 A | 11/1996 | Nakajima et al. | |
| 5,607,472 A | 3/1997 | Thompson | |
| 5,611,968 A | 3/1997 | Grisoni et al. | |
| 5,647,865 A | 7/1997 | Swinger | |
| 5,674,282 A | 10/1997 | Cumming | |
| 5,686,414 A | 11/1997 | Scannon | |
| 5,699,142 A | 12/1997 | Lee et al. | |
| 5,716,403 A | 2/1998 | Tran et al. | |
| 5,800,532 A | 9/1998 | Lieberman | |
| 5,837,156 A | 11/1998 | Cumming | |
| 5,843,187 A | 12/1998 | Bayers | |
| 5,873,879 A | 2/1999 | Figueroa et al. | |
| 5,919,230 A | 7/1999 | Sambursky | |
| 5,944,725 A | 8/1999 | Cicenas et al. | |
| 5,968,094 A | 10/1999 | Werblin et al. | |
| 5,984,914 A | 11/1999 | Cumming | |
| 6,007,579 A | 12/1999 | Lipshitz et al. | |
| 6,013,101 A | 1/2000 | Israel | |
| 6,015,435 A | 1/2000 | Valunin et al. | |
| 6,027,531 A | 2/2000 | Tassignon | |
| 6,051,024 A | 4/2000 | Cumming | |
| 6,066,171 A | 5/2000 | Lipshitz et al. | |
| 6,066,172 A | 5/2000 | Huo et al. | |
| 6,113,633 A | 9/2000 | Portney | |
| 6,129,760 A | 10/2000 | Fedorov et al. | |
| 6,161,544 A | 12/2000 | DeVore | |
| 6,164,282 A | 12/2000 | Gwon et al. | |
| 6,176,878 B1 * | 1/2001 | Gwon et al. | 623/6.37 |
| 6,179,870 B1 * | 1/2001 | Sourdille et al. | 623/6.39 |
| 6,193,750 B1 | 2/2001 | Cumming | |
| 6,197,058 B1 | 3/2001 | Portney | |
| 6,197,059 B1 * | 3/2001 | Cumming | 623/6.39 |
| 6,217,612 B1 | 4/2001 | Woods | |
| 6,299,641 B1 | 10/2001 | Woods | |
| 6,302,911 B1 | 10/2001 | Hanna | |
| 6,322,589 B1 * | 11/2001 | Cumming | 623/6.44 |
| 6,342,073 B1 | 1/2002 | Cumming et al. | |
| 6,387,126 B1 | 5/2002 | Cumming | |
| 6,391,056 B2 | 5/2002 | Cumming | |
| 6,406,494 B1 | 6/2002 | Laguette et al. | |
| 6,409,763 B1 | 6/2002 | Brady | |
| 6,413,276 B1 | 7/2002 | Werblin | |
| 6,419,697 B1 | 7/2002 | Kelman | |
| 6,423,094 B1 | 7/2002 | Sarfarazi | |
| 6,443,985 B1 | 9/2002 | Woods | |
| 6,451,056 B1 | 9/2002 | Cumming | |
| 6,461,384 B1 | 10/2002 | Hoffmann et al. | |
| 6,488,708 B2 | 12/2002 | Sarfarazi | |
| 6,494,911 B2 | 12/2002 | Cumming | |
| 6,497,708 B1 | 12/2002 | Cumming | |
| 6,503,275 B1 | 1/2003 | Cumming | |
| 6,503,276 B2 | 1/2003 | Lang et al. | |
| 6,517,577 B1 | 2/2003 | Callahan et al. | |
| 6,524,340 B2 * | 2/2003 | Israel | 623/6.44 |
| 6,540,353 B1 | 4/2003 | Dunn | |
| 6,558,420 B2 | 5/2003 | Green | |
| 6,613,343 B2 | 9/2003 | Dillingham et al. | |
| 6,616,691 B1 | 9/2003 | Tran | |
| 6,616,692 B1 | 9/2003 | Glick et al. | |
| 6,638,305 B2 | 10/2003 | Laguette | |
| 6,638,306 B2 | 10/2003 | Cumming | |
| 6,645,245 B1 | 11/2003 | Preussner | |
| 6,660,035 B1 | 12/2003 | Lang et al. | |
| 6,660,036 B2 | 12/2003 | Cumming | |
| 6,685,741 B2 | 2/2004 | Landreville et al. | |
| 6,695,881 B2 | 2/2004 | Peng et al. | |
| 6,749,634 B2 | 6/2004 | Hanna | |
| 6,767,363 B1 | 7/2004 | Bandhauer et al. | |
| 6,849,091 B1 | 2/2005 | Cumming | |

(56) References Cited

U.S. PATENT DOCUMENTS

| | | |
|---|---|---|
| 6,858,040 B2 | 2/2005 | Nguyen et al. |
| 6,881,225 B2 | 4/2005 | Okada |
| 6,884,263 B2 | 4/2005 | Valyunin |
| 6,921,416 B2 | 7/2005 | Khoury |
| 6,926,736 B2 | 8/2005 | Peng |
| 6,932,839 B1 | 8/2005 | Kamerling et al. |
| 6,969,403 B2 | 11/2005 | Peng |
| 6,972,033 B2 | 12/2005 | McNicholas |
| 7,018,409 B2 | 3/2006 | Glick |
| 7,025,783 B2 | 4/2006 | Brady |
| 7,037,338 B2 | 5/2006 | Nagamoto |
| 7,048,760 B2 | 5/2006 | Cumming |
| 7,097,660 B2 | 8/2006 | Portney |
| 7,125,422 B2 | 10/2006 | Woods et al. |
| 7,150,759 B2 | 12/2006 | Paul et al. |
| 7,150,760 B2 | 12/2006 | Zhang |
| 7,229,475 B2 | 6/2007 | Glazier |
| 7,229,476 B2 | 6/2007 | Azar |
| 7,300,464 B2 | 11/2007 | Tran |
| 7,326,246 B2 | 2/2008 | Brady |
| 7,341,599 B1 | 3/2008 | Peyman |
| 7,435,258 B2 | 10/2008 | Blake |
| 7,435,259 B2 | 10/2008 | Cumming |
| 7,553,327 B2 | 6/2009 | Cumming |
| 7,662,180 B2 | 2/2010 | Paul et al. |
| 7,763,070 B2 | 7/2010 | Cumming |
| 7,837,730 B2 | 11/2010 | Cumming |
| 7,981,155 B2 | 7/2011 | Cumming |
| 7,985,253 B2 | 7/2011 | Cumming |
| 8,038,711 B2 | 10/2011 | Clarke |
| 8,080,056 B2 | 12/2011 | Cumming |
| 8,100,965 B2 | 1/2012 | Cumming et al. |
| 8,109,998 B2 | 2/2012 | Cumming |
| 8,163,015 B2 | 4/2012 | Cumming |
| 8,216,308 B2 | 7/2012 | Blake et al. |
| 8,388,608 B1 | 3/2013 | Kaluzna |
| 8,523,942 B2 | 9/2013 | Cumming |
| 8,734,512 B2 | 5/2014 | Cumming |
| 8,764,823 B2 * | 7/2014 | Cumming .................. 623/6.43 |
| 9,034,036 B2 | 5/2015 | Cumming |
| 2001/0001836 A1 | 5/2001 | Cumming |
| 2002/0120329 A1 | 8/2002 | Lang et al. |
| 2002/0138140 A1 | 9/2002 | Hanna |
| 2003/0060881 A1 | 3/2003 | Glick et al. |
| 2003/0078658 A1 | 4/2003 | Zadno-Azizi |
| 2003/0097177 A1 * | 5/2003 | Tran ............................. 623/6.47 |
| 2003/0109925 A1 | 6/2003 | Ghazizadeh et al. |
| 2003/0135272 A1 | 7/2003 | Brady et al. |
| 2003/0142269 A1 | 7/2003 | Cumming |
| 2003/0171808 A1 | 9/2003 | Phillips |
| 2003/0171809 A1 | 9/2003 | Phillips |
| 2003/0187505 A1 | 10/2003 | Liao |
| 2003/0199977 A1 | 10/2003 | Cumming |
| 2003/0204257 A1 | 10/2003 | Southard |
| 2004/0002757 A1 | 1/2004 | Lai et al. |
| 2004/0015236 A1 | 1/2004 | Sarfarazi |
| 2004/0082993 A1 | 4/2004 | Woods |
| 2004/0082994 A1 | 4/2004 | Woods et al. |
| 2004/0111152 A1 | 6/2004 | Kelman |
| 2004/0148023 A1 | 7/2004 | Shu |
| 2004/0215207 A1 | 10/2004 | Cumming |
| 2004/0215340 A1 | 10/2004 | Messner et al. |
| 2004/0220666 A1 | 11/2004 | Cumming |
| 2004/0243232 A1 | 12/2004 | Cumming |
| 2004/0249456 A1 | 12/2004 | Cumming |
| 2005/0021140 A1 | 1/2005 | Liao |
| 2005/0027354 A1 | 2/2005 | Brady et al. |
| 2005/0075732 A1 | 4/2005 | Israel |
| 2005/0096741 A1 | 5/2005 | Cumming |
| 2005/0107875 A1 | 5/2005 | Cumming |
| 2005/0125058 A1 | 6/2005 | Cumming et al. |
| 2005/0137703 A1 | 6/2005 | Chen |
| 2005/0267576 A1 | 12/2005 | Cumming |
| 2005/0288784 A1 | 12/2005 | Peyman |
| 2006/0064077 A1 | 3/2006 | Peyman |
| 2006/0064162 A1 | 3/2006 | Klima |
| 2006/0100704 A1 * | 5/2006 | Blake et al. .................. 623/6.37 |
| 2006/0111776 A1 | 5/2006 | Glick et al. |
| 2006/0116764 A1 | 6/2006 | Simpson |
| 2006/0149369 A1 | 7/2006 | Cumming et al. |
| 2007/0021832 A1 | 1/2007 | Nordan |
| 2007/0032867 A1 | 2/2007 | Cumming |
| 2007/0129800 A1 | 6/2007 | Cumming |
| 2007/0129803 A1 | 6/2007 | Cumming et al. |
| 2007/0135915 A1 | 6/2007 | Klima |
| 2007/0142908 A1 | 6/2007 | Xu |
| 2007/0198084 A1 | 8/2007 | Cumming et al. |
| 2007/0244472 A1 | 10/2007 | Kuhn et al. |
| 2008/0027538 A1 | 1/2008 | Cumming |
| 2008/0027539 A1 | 1/2008 | Cumming |
| 2008/0027540 A1 | 1/2008 | Cumming |
| 2008/0046077 A1 | 2/2008 | Cumming |
| 2008/0086208 A1 | 4/2008 | Nordan |
| 2008/0154362 A1 | 6/2008 | Cumming |
| 2008/0281415 A1 | 11/2008 | Cumming |
| 2008/0281416 A1 | 11/2008 | Cumming |
| 2008/0288066 A1 | 11/2008 | Cumming |
| 2008/0294254 A1 | 11/2008 | Cumming et al. |
| 2008/0319545 A1 * | 12/2008 | Cumming .................... 623/6.11 |
| 2009/0005866 A1 | 1/2009 | Cumming |
| 2009/0234449 A1 * | 9/2009 | De Juan et al. ............... 623/6.22 |
| 2009/0248154 A1 | 10/2009 | Dell |
| 2010/0004742 A1 | 1/2010 | Cumming |
| 2010/0057202 A1 | 3/2010 | Bogaert |
| 2011/0313519 A1 | 12/2011 | Cumming |
| 2011/0313525 A1 | 12/2011 | Cumming |
| 2012/0296424 A1 | 11/2012 | Betser |
| 2013/0073039 A1 | 3/2013 | Mirlay |
| 2013/0231742 A1 | 9/2013 | Deacon et al. |
| 2014/0088699 A1 | 3/2014 | Cumming |
| 2014/0094909 A1 | 4/2014 | Cumming |
| 2014/0155871 A1 | 6/2014 | Cumming |
| 2014/0172093 A1 | 6/2014 | Cumming |
| 2015/0012088 A1 | 1/2015 | Cumming |
| 2015/0073550 A1 | 3/2015 | Cumming |
| 2015/0088254 A1 | 3/2015 | Cumming |
| 2015/0182327 A1 | 7/2015 | Cumming |
| 2015/0182328 A1 | 7/2015 | Cumming |
| 2015/0245904 A1 | 9/2015 | Cumming |
| 2015/0245905 A1 | 9/2015 | Cumming |
| 2015/0272726 A1 | 10/2015 | Cumming |

FOREIGN PATENT DOCUMENTS

| | | |
|---|---|---|
| DE | 3626869 | 2/1988 |
| FR | 2728458 | 6/1996 |
| FR | 2728459 | 6/1996 |
| FR | 2734472 | 11/1996 |
| FR | 2765797 | 1/1999 |
| FR | 2991572 | 12/2013 |
| GB | 2171912 | 9/1986 |
| GB | 2226246 | 6/1990 |
| JP | 2003-190193 | 7/2003 |
| SU | 1123685 | 11/1984 |
| WO | WO 93/05733 | 4/1993 |
| WO | WO 01/19288 | 3/2001 |
| WO | WO 01/19289 | 3/2001 |
| WO | WO 03/017873 | 3/2003 |
| WO | WO 2007/037180 | 4/2007 |
| WO | WO 2009/048656 | 4/2009 |
| WO | WO 2009/086511 | 7/2009 |
| WO | WO 2011/151839 | 12/2011 |

OTHER PUBLICATIONS

Final Office Action for U.S. Appl. No. 13/111,599 dated May 2, 2013 in 10 pages.
Final Office Action for U.S. Appl. No. 13/155,327 dated Dec. 10, 2012 in 10 pages.
Final Office Action for U.S. Appl. No. 13/953,605 dated Sep. 25, 2014 in 17 pages.
International Search Report and Written Opinion for PCT/US13/61452 dated Feb. 24, 2014 in 11 pages.

(56) References Cited

OTHER PUBLICATIONS

Office Action for U.S. Appl. No. 13/017,189 dated May 9, 2013 in 9 pages.
Office Action for U.S. Appl. No. 13/111,599 dated Jan. 2, 2013 in 11 pages.
Office Action for U.S. Appl. No. 13/111,599 dated Sep. 5, 2014 in 13 pages.
Office Action for U.S. Appl. No. 13/155,327 dated Jul. 20, 2012 in 7 pages.
Office Action for U.S. Appl. No. 13/155,327 dated Apr. 26, 2013 in 7 pages.
Office Action for U.S. Appl. No. 13/953,605 dated May 20, 2014 in 9 pages.
Office Action for U.S. Appl. No. 13/891,088 dated Aug. 13, 2014 in 25 pages.
Office Action for U.S. Appl. No. 13/910,076 dated Nov. 7, 2014 in 12 pages.
Office Action for U.S. Appl. No. 14/143,162 dated Aug. 4, 2014 in 18 pages.
Office Action for U.S. Appl. No. 14/257,933 dated Oct. 31, 2014 in 9 pages.
Response to Office Action for U.S. Appl. No. 13/017,189 dated Aug. 8, 2013 in 5 pages.
Response to Office Action for U.S. Appl. No. 13/111,599 dated Apr. 9, 2013 in 6 pages.
Response to Office Action for U.S. Appl. No. 13/111,599 dated Jul. 30, 2013 in 6 pages.
Response to Office Action for U.S. Appl. No. 13/155,327 dated Oct. 26, 2012 in 5 pages.
Response to Office Action for U.S. Appl. No. 13/155,327 dated Apr. 10, 2013 in 5 pages.
Response to Office Action for U.S. Appl. No. 13/155,327 dated Jul. 25, 2013 in 5 pages.
Response to Office Action for U.S. Appl. No. 13/953,605 dated Aug. 19, 2014 in 7 pages.
Response to Office Action for U.S. Appl. No. 13/891,088 dated Dec. 15, 2014 in 8 pages.
Dykstra, M., et al. Biological Electron Microscopy: Theory, Techniques, and Troubleshooting, 2003, p. 81.
Response to Final Office Action for U.S. Appl. No. 13/017,189 dated Dec. 18, 2014 in 10 pages.
Response to Office Action for U.S. Appl. No. 13/111,599 dated Jan. 6, 2015 in 13 pages.
Response to Final Office Action for U.S. Appl. No. 13/953,605 dated Dec. 18, 2014 in 12 pages.
Response to Office Action for U.S. Appl. No. 13/910,076 dated Feb. 9, 2015 in 10 pages.
Response to Office Action for U.S. Appl. No. 14/143,612 dated Jan. 5, 2015 in 8 pages.
Response to Office Action for U.S. Appl. No. 14/257,933 dated Feb. 2, 2015 in 10 pages.
Final Office Action for U.S. Appl. No. 13/017,189 dated Jan. 13, 2015 in 20 pages.
Final Office Action for U.S. Appl. No. 13/111,599 dated Feb. 6, 2015 in 21 pages.
Final Office Action for U.S. Appl. No. 14/274,352 dated Jun. 8, 2015 in 27 pages.
Final Office Action for U.S. Appl. No. 13/891,088 dated Jul. 2, 2015 in 17 pages.
Final Office Action for U.S. Appl. No. 14/035,813 dated Sep. 30, 2015 in 26 pages.
Final Office Action for U.S. Appl. No. 14/143,612 dated Mar. 20, 2015 in 14 pages.
Final Office Action for U.S. Appl. No. 14/257,933 dated Mar. 19, 2015 in 23 pages.
First Action Interview Pre-Interview Communication for U.S. Appl. No. 14/741,230 dated Jul. 30, 2015 in 5 pages.
International Search Report and Written Opinion for PCT/US2014/057037 dated Jan. 20, 2015 in 12 pages.
International Search Report and Written Opinion for PCT/US2014/072518 dated Jul. 23, 2015 in 15 pages.
Internet Archive Wayback Machine; Crystalens—Is Crystalens right for you?; downloaded from http://web.archive.org/web/20141025080709/http://crystalens.com/en-us/iscrystalensrightforyou.aspx (Archived Oct. 25, 2014; printed on Aug. 12, 2015).
Office Action for U.S. Appl. No. 13/111,599 dated Jun. 26, 2015 in 12 pages.
Office Action for U.S. Appl. No. 14/270,166 dated Mar. 3, 2015 in 19 pages.
Office Action for U.S. Appl. No. 14/712,827 dated Oct. 6, 2015 in 38 pages.
Office Action for U.S. Appl. No. 14/274,352 dated Feb. 12, 2015 in 10 pages.
Office Action for U.S. Appl. No. 13/910,076 dated Apr. 10, 2015 in 26 pages.
Office Action for U.S. Appl. No. 14/035,821 dated Apr. 13, 2015 in 33 pages.
Office Action for U.S. Appl. No. 14/035,813 dated Mar. 26, 2015 in 16 pages.
Office Action for U.S. Appl. No. 14/143,162 dated Jul. 27, 2015 in 13 pages.
Office Action for U.S. Appl. No. 14/257,933 dated Aug. 31, 2015 in 14 pages.
Office Action for U.S. Appl. No. 14/584,188 dated Oct. 6, 2015 in 21 pages.
Response to Final Office Action for U.S. Appl. No. 13/017,189 filed Dec. 18, 2014 in 10 pages.
Response to Final Office Action for U.S. Appl. No. 13/111,599 filed Jan. 6, 2015 in 13 pages.
Response to Office Action for U.S. Appl. No. 13/111,599 filed Jun. 8, 2015 in 12 pages.
Response to Final Office Action for U.S. Appl. No. 13/953,605 filed Dec. 18, 2014 in 12 pages.
Response to Office Action for U.S. Appl. No. 14/274,352 filed May 12, 2015 in 10 pages.
Response to Office Action for U.S. Appl. No. 14/274,352 filed Oct. 22, 2015 in 14 pages.
Response to Office Action for U.S. Appl. No. 13/910,076 filed Feb. 9, 2015 in 10 pages.
Response to Office Action for U.S. Appl. No. 13/910,076 filed Oct. 9, 2015 in 15 pages.
Response to Office Action for U.S. Appl. No. 14/035,821 filed Oct. 12, 2015 in 15 pages.
Response to Office Action for U.S. Appl. No. 14/035,813 filed Jul. 27, 2015 in 10 pages.
Response to Office Action for U.S. Appl. No. 14/035,813 filed Oct. 20, 2015 in 13 pages.
Response to Office Action for U.S. Appl. No. 14/143,612 filed Jan. 5, 2015 in 8 pages.
Response to Office Action for U.S. Appl. No. 14/143,612 filed Jul. 17, 2015 in 8 pages.
Response to Office Action for U.S. Appl. No. 14/257,933 filed Feb. 2, 2015 in 10 pages.
Response to Office Action for U.S. Appl. No. 14/257,933 filed Jul. 17, 2015 in 10 pages.
Final Office Action for U.S. Appl. No. 13/017,189 dated Oct. 28, 2015 in 9 pages.
Preliminary Amendment for U.S. Appl. No. 14/741,230 dated Oct. 14, 2015 in 12 pages.
Response to Final Office Action for U.S. Appl. No. 13/017,189, filed Apr. 13, 2015 in 8 pages.
Response to Office Action for U.S. Appl. No. 14/270,166, filed Aug. 3, 2015 in 12 pages.
Supplemental Response to Final Office Action for U.S. Appl. No. 13/017,189, filed Jun. 12, 2015 in 8 pages.

* cited by examiner

VITREOUS COMPRESSING PLATE HAPTIC

CROSS-REFERENCE TO RELATED APPLICATIONS

This application is based on and claims the benefit of the filing of U.S. Provisional Patent Application No. 61/398,107, filed Jun. 21, 2010; U.S. Provisional Patent Application No. 61/398,098, filed Jun. 21, 2010; U.S. Provisional Patent Application No. 61/398,115, filed Jun. 21, 2010; and U.S. Provisional Patent Application No. 61/398,099, filed Jun. 21, 2010, the contents and disclosure of which are fully incorporated herein by reference.

This application is related to U.S. Non-Provisional Patent Application No. 13/017,189, filed Feb. 14, 2011, the contents and disclosure of which is fully incorporated herein by reference.

BACKGROUND OF THE INVENTION

Accommodating Intraocular Lenses were developed in the early 1900's and have been sold in Europe for the last ten years and later in the U.S. They function by means of forward movement of the optic upon constriction of the ciliary muscle which increases the pressure in the posterior part of the eye with a simultaneous decrease in pressure in the front part of the eye pressure. The reverse pressure changes take place upon relaxation of the ciliary muscle, which results in the backwards movement of the lens for distance vision. The forward movement of the lens optic enables the patient implanted with the lens to automatically change their vision from distance to see at intermediate and near.

The first intraocular lenses developed by Harold Ridley were implanted in patients at St. Thomas' Hospital in London in 1949. The lenses were made of "perspex" (polymethylmethacrylate) and were large, heavy, rigid and biconvex. The complication rate was high since the specific gravity of PMMA was heavier than that of the aqueous that they were surrounded by, and they tended to de-center, or dislocate. This was just one of the complications of this first design. These lenses were placed in the eye behind the iris and in front of the posterior capsule of the human lens after the cataract had been removed, leaving behind the posterior capsule.

Subsequent lens designs by Epstein, Binkhorst and Worst attached the lens to the iris. This, along with anterior chamber lenses reduced the complication rate but it was not until Shearing developed a lens to be implanted into the empty capsular bag, putting the lens optic, once again back where it belonged, behind the iris, that there was a significant reduction in complications. This posterior chamber lens design was the first to have open loops attached to the optic, which helped to center and fixate the lens within the capsular bag by capturing the loops within the bag by means of fibrosis of the anterior capsule remnants to the posterior capsule over the flexible loops. These loops were called haptics.

Many iterations of this design followed. All the optics of these lenses were made of rigid PMMA. In the 1970's Mazzocco developed a single piece posterior chamber lens made from silicone that could be folded. This lens was molded as one piece, had no loops, and had what are now called "plate haptics", which replaced the loops. At the time phacoemulsification had been developed and the cataract could be extracted through a 3-4 mm incision. However, since the earlier lenses had been made of rigid PMMA and had an optic diameter of 5-6 mm, the wound had to be enlarged to allow the lens to be inserted into the eye and had to be sutured. The advent of Mazzocco's foldable lens changed all this. It enabled foldable lenses to be inserted into the eye, folded, through a 3-4 mm tunnel incision, that now needs no suturing.

The word "haptic" has been used to describe an attachment to intraocular lenses. The original intraocular lens consisted of a single optic. These lenses frequently de-centered. It was discovered that there was a need to center and fixate the lens optic in the vertical meridian of the eye. The first attachments to the optic were called "haptics". They consisted of multiple flexible loops of various designs, J loops, C loops, closed loops and flexible radial arms.

Later, these loops which became commonly referred to as "haptics" were replaced in some lens designs with flat homogeneous plates, called "plate haptics". The plate haptic design has two main advantages over loop lenses. First, if they have a plate length of 10.5 to 11.5 mm they vault backwards when confined within the approximate 10.5 mm diameter and 5.0 mm deep space that remains within the human capsular bag after extracting the cataract. Second, their location along the axis of the eye is more consistent than that of loop lenses. These two properties of plate lenses reduce the incidence of the major post-operative complications of cataract surgery, which are retinal detachments and cystoid macular edema, and because of the more consistent location of the lens optic along the axis of the eye, the uncorrected post-operative visual acuities are superior to those of loop lenses.

During constriction of the circular ciliary muscle its diameter decreases and it compresses distal ends of opposing plate haptics which then move centrally. Since the uni-planar plate haptics tend to naturally vault posteriorly when placed within the capsular bag the proximal end of the plates attached to the lens optic move posteriorly. This posterior movement helps to increase the vitreous cavity pressure behind the lens and the lens optic, and pushes the lens optic anteriorly. This increase in vitreous cavity pressure, with a simultaneous decrease in pressure in the anterior chamber of the eye is a natural occurrence in the human eye with accommodation to see at near. However, due to its construction, the lens optic of a traditional plate haptic lens is limited in its response to the change in vitreous pressure.

Furthermore, when a plate haptic lens is placed within the capsular bag of the eye the peripheral circumferential remains of the anterior capsule and the posterior capsule of the human capsular bag, fibrose over the distal ends of the plates. The area of fibrosis can vary and sometimes covers only the distal 1.0 mm of the tip of the plate. With inadequate coverage of the distal ends of the plates the plate haptics can sometimes dislocate, one of the plates vaulting forwards to configure the lens in a "Z" shape configuration.

SUMMARY OF THE INVENTION

An accommodating intraocular lens design according to an embodiment of the present invention is described that overcomes the deficiencies of present designs noted above.

A flat, longitudinal accommodating intraocular lens is provided, having distinct separate plate haptics partially surrounding a lens optic.

By extending the lateral surface area of the plates adjacent the optic to partially surround the optic, the haptic presses posteriorly on the vitreous immediately adjacent to and almost surrounding the lens optic. The extended part of the plate increases the area of contact of the plate haptic with the vitreous face, on either side of the optic and enhances the effect of the pressure changes within the eye that occur naturally with constriction and relaxation of the ciliary muscle that occurs with accommodation.

A second feature of this plate design is a small triangular extension of distal-lateral ends of the plate haptics, thereby widening the distal end of the plate haptic by 0.75-1.5 mm on either side of each plate haptic. This allows for a greater area of contact between the fibrosed capsule and the tip of the plates to reduce the incidence and complication of "Z" formations.

Other features and advantages of the present invention will become apparent from the following more detailed description, taken in conjunction with the accompanying drawings, which illustrate, by way of example, the principles of the presently described apparatus and method of its use.

BRIEF DESCRIPTION OF THE SEVERAL VIEWS OF THE DRAWING(S)

Illustrated in the accompanying drawing(s) is at least one of the best mode embodiments of the present invention In such drawing(s):

DETAILED DESCRIPTION OF THE PREFERRED EMBODIMENTS

The above described drawing figures illustrate the described invention and method of use in at least one of its preferred, best mode embodiment, which is further defined in detail in the following description. Those having ordinary skill in the art may be able to make alterations and modifications to what is described herein without departing from its spirit and scope. Therefore, it should be understood that what is illustrated is set forth only for the purposes of example and should not be taken as a limitation on the scope of the present apparatus and its method of use.

Figure 1:
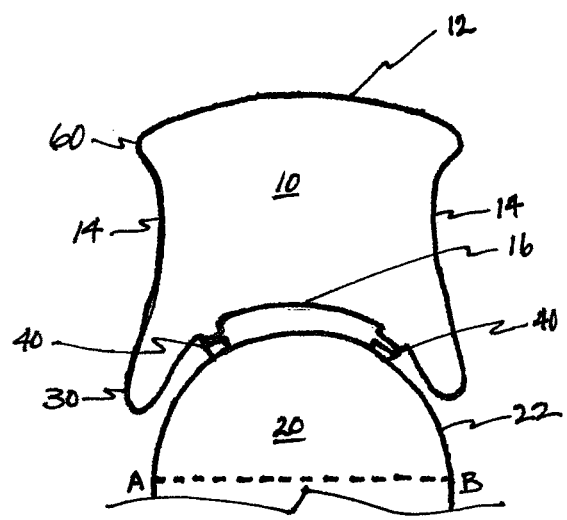
FIG. 1 illustrates a top view of a vitreous compressing plate haptic according to an embodiment of the present invention.

As illustrated in FIG. 1, an intraocular accommodating lens may comprise at least one plate haptic 10 and a lens optic 20.

The plate haptic 10 may comprise a distal portion 12, opposing lateral portions 14, and a proximal portion 16. In at least one preferred embodiment, the plate haptic 10 may be substantially or partially constructed of flexible material, such as silicone, acrylic, hydrogel, and/or similar materials known in the art.

The plate haptic 10 may be of solid, unitary construction, and may have tapered, rounded or parallel edges. In some embodiments, the plate haptic 10 may be between 5.0 and 6.0 mm in width, and between 0.2 to 0.75 mm in thickness. Preferably, the longitudinal length or circumference diameter of the plate haptic 10 may be between 10.0 to 12.0 mm.

Figure 2:
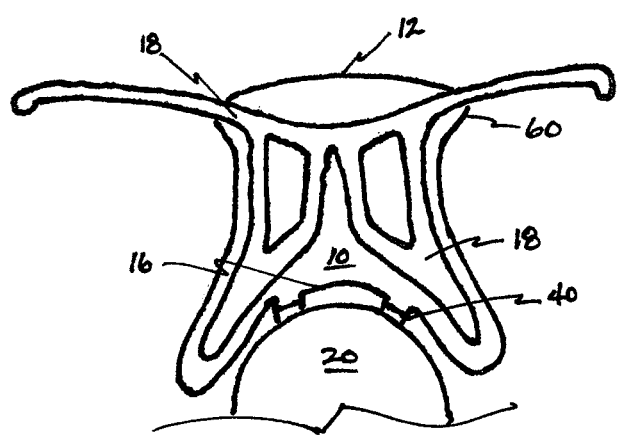
FIG. 2 illustrates a top view of a vitreous compressing plate haptic according to an embodiment of the present invention.
Figure 3:
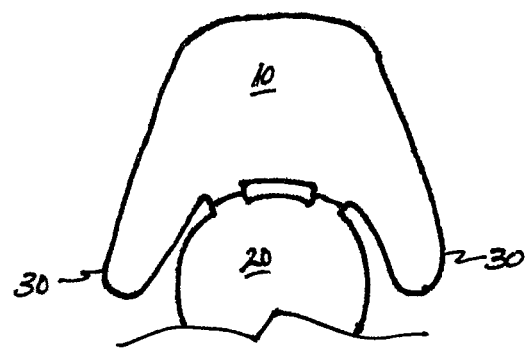
FIG. 3 illustrates a top view of a vitreous compressing plate haptic according to an embodiment of the present invention.

The lens optic 20 may comprise a periphery 22 and a transverse diameter defined by points A and B, as shown in FIGS. 1-3. In at least one preferred embodiment, the proximal portion 16 of the plate haptic is substantially parallel to the periphery 22 of the optic and contoured thereto. In at least one preferred embodiment, the lens optic 20 comprises at least one of: solid, single, multifocal, Fresnell, toric, biconvex, plano-convex refractive, diffractive or liquid filled optics. In at least one preferred embodiment, the lens optic 20 may be substantially or partially constructed of flexible material, such as silicone, acrylic, hydrogel, and/or similar materials known in the art.

As illustrated in FIG. 2, in at least one preferred embodiment, the plate haptic 10 may comprise a chassis 18. The chassis 18 may be operable to permit flexion of the plate haptic 10 in the longitudinal direction and to substantially resist and prevent flexion of the plate haptic 10 in the transverse direction. This discriminatory flexion permits the lens to be inserted into an eye in a compact state while resisting bending in response to vitreous pressure from the eye once it is inserted.

In at least one preferred embodiment, the chassis 18 may be a semi-rigid chassis 18 constructed of at least one of: silicone, acrylic, hydrogel, polyamide, prolene, PMMA and titanium. It should be observed that according to at least one preferred embodiment, the chassis 18 may be constructed of the same material as either or both of the plate haptic 10 and the lens optic 20. In some embodiments, the chassis 18 may consist of portions of increased thickness of the plate haptic 10. In shape, the chassis 18 preferably comprises an irregular web throughout the plate haptic 10, however, regular and repeated frame elements are specifically contemplated.

In at least one preferred embodiment, the proximal portion 16 of the plate haptic 10 comprises a flexible junction 40 connecting the lens optic 20 to the plate haptic 10, as shown in FIGS. 1-2. The flexible junction 40 may be operable to reduce the resistance of the lens optic 20 to a change in vitreous cavity pressure, thereby allowing more movement of the lens optic 20 along the axis of the eye.

The flexible junction 40 may comprise a single strap, or may comprise a plurality of spaced apart flexible straps. The strap or straps may extend substantially longitudinally from the proximal portion 16 of the plate haptic 10 and connect the plate haptic 10 to the periphery 22 of the lens optic 20. Alternatively, the strap or straps may extend substantially radially from the periphery 22 of the lens optic 20 and connect the lens optic 20 to the proximal portion 16 of the plate haptic 10. As illustrated in FIG. 1, each strap may have one or more hinges 50 laterally traversing the strap and weakening the strap 40 so as to promote stretching and flexion thereat. The hinge may consist of a single groove. Alternatively, the hinge may consist of two or more directly or indirectly opposing grooves.

Returning to FIG. 1, in at least one preferred embodiment, each lateral portion 14 along with the proximal portion 16 forms an appendage 30. Thus, the plate haptic 10 may comprise a plurality of appendages 30, and preferably comprises two appendages 30 that together partially surround the lens optic 20. The appendage may be paddle shaped but is not limited thereto and should be understood through its functionality. As the ciliary muscle contracts it exerts an inwardly radial end-to-end pressure on opposing plate haptics 10 which are then forced centrally and posteriorly. Because the appendages 30 partially surround the optic 20, increased pressure is exerted by the vitreous cavity, thereby increasing displacement of the lens optic 20 along the axis of the eye.

Figure 4:
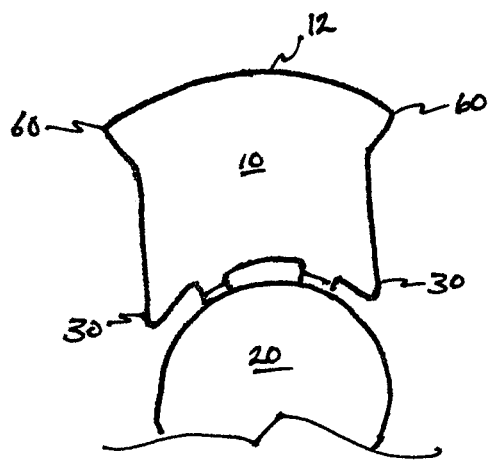
FIG. 4 illustrates a top view of a vitreous compressing plate haptic according to an embodiment of the present invention.

In some embodiments, the appendages 30 may extend from the proximal portion 16 at an angle that is substantially between complete lateral extension and complete longitudinal extension. Alternatively, as shown in FIG. 4, the appendages 30 may extend from the proximal portion 16 at an angle that is substantially longitudinal. In at least one preferred embodiment, the appendages 30 are positioned substantially more laterally than the straps.

Turning now to FIG. 3, in some embodiments, the lateral extension of the appendages 30 may be greater than the transverse diameter of the lens optic 20. In other words, the appendage may extend out beyond an imaginary line tangent to the lateral most point(s) of the lens optic 20 periphery 22. In some embodiments, the lateral extension of the appendages 30 may be such that the lateral portions 14 are substantially co-extensive with the transverse diameter of the lens optic 20, as shown in FIG. 4.

As discussed above, each appendage 30 is formed of the lateral portion 14 and proximal portion 16. In some embodiments, the lateral portions 14 of opposing appendages 30 may be substantially non-convergent. In other words, the lateral portion 14 may be approximated by lines which, if extended roughly in the direction of the lens optic 20, would be substantially non-convergent. In at least one preferred embodiment, the lateral portion 14 may be substantially divergent, as shown in FIG. 3. In at least one preferred embodiment, they may be substantially parallel, as shown in FIG. 4.

The appendages 30 may be of any shape that substantially extends the contact area of the plate haptic 10 with the capsular bag thereby increasing vitreous pressure response. As illustrated in FIG. 4, in at least one preferred embodiments, the appendage 30 may be partially triangular in shape—the lateral portion 14 and proximal portion 16 comprising two sides of a triangle. As illustrated in FIGS. 1-3, in at least one other preferred embodiment the appendage 30 may be curved and may be partially elliptical in shape. For example, the appendage may be substantially paddle, or tear-drop shaped—the lateral portion 14 and proximal portion 16 approximating the curve. In some embodiments, the appendage 30 may be between 2.0 to 7.0 mm in width. In some embodiments, the appendage 30 may be between 0.02 to 0.75 mm in thickness.

The appendages 30 may be of fully or partially rigid construction. In some embodiments, the appendages 30 are partially or wholly constructed of flexible material such as: silicone, acrylic, hydrogel, and the like. In some embodiments the appendages 30 are partially or wholly constructed of substantially rigid or semi-rigid material such as: polyamide, prolene, PMMA, titanium and the like. In some embodiments, the appendages 30 at least partially include at least a portion of the chassis 18, as shown in FIG. 2.

Turning now to FIGS. 1-4, in at least one preferred embodiment, the distal end is convex so as to increase a contact surface area. Furthermore, in at least one preferred embodiment, each lateral portion 14 along with the distal portion 12 forms a projection 60, as shown in FIGS. 1-2 and 4. Thus, the plate haptic 10 may comprise a plurality of projections 60, and preferably comprises two projections 60 that may extend substantially laterally from the distal portion 12. The projections 60 may further increase the area of contact between the distal portion 12 of the plate haptic 10 and the capsular bag of the eye. Preferably, the projections 60, in combination with the distal portion 12 may substantially occupy the cul de sac of the capsular bag. In at least one embodiment, the projections 60 may be partially triangular, elliptical, curved, or of any shape operable to increase the contact area. The projections 60 may also comprise a portion of the chassis 18, as shown in FIG. 2.

In at least one embodiment, the intraocular accommodating lens comprises a plurality, and preferably a pair, of opposing plate haptics 10, each connected to the lens at respective flexible junctions 40. In some embodiments, however, the intraocular accommodating lens comprises a single plate haptic 10 opposing a non-plate haptic 10 of a type known in the art.

The enablements described in detail above are considered novel over the prior art of record and are considered critical to the operation of at least one aspect of the invention and to the achievement of the above described objectives. The words used in this specification to describe the instant embodiments are to be understood not only in the sense of their commonly defined meanings, but to include by special definition in this specification: structure, material or acts beyond the scope of the commonly defined meanings Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that the named inventor believes that the claimed subject matter is what is intended to be patented.

What is claimed is:
1. An intraocular lens comprising:
a lens optic; and
a pair of plate haptics coupled to the lens optic, each of the plate haptics having a proximal edge, a distal edge, and opposing lateral edges extending from the proximal edge to the distal edge, the proximal edge of each plate haptic being closer to the optic than the distal edge,
wherein each plate haptic comprises a pair of appendages at least partially surrounding the optic and entirely displaced from a distal end of said plate haptic, each appendage formed by a portion of one of the lateral edges and a portion of the proximal edge, a proximal end portion of each appendage being spaced apart from the lens optic,
wherein a longitudinal axis of the intraocular lens extends through each of the plate haptics, a transverse diameter of the lens optic being perpendicular to the longitudinal axis of the intraocular lens,
wherein a width is measured between medial edges of the proximal end portions of the appendages of the same haptic, the width being greater than the transverse diameter of the lens optic,
wherein each appendage comprises a plate appendage and is co-planar and unitary or co-extensive with said appendage's respective haptic, the plate appendage being a proximal cantilevered extension of said appendage's respective haptic, and each appendage being spaced laterally and radially outwardly from the optic and terminating in a convex end portion, wherein each appendage extends at a non-convergent angle with respect to the other appendage of the same haptic and has a medial edge contoured with respect to the optic, wherein each haptic and said haptic's associated pair of appendages together only partially surrounding the optic, each appendage being curved to be partially elliptical in shape and having a width between 2.0 and 7.0 mm, wherein the pair of appendages extending from each haptic form a maximum transverse dimension of the intraocular lens that is greater than the transverse diameter of the lens optic, a longitudinal dimension of the intraocular lens measured along the longitudinal axis of the intraocular lens being greater than the maximum transverse dimension.

2. The lens of claim 1, wherein the opposing lateral edges are non-convergent.

3. The lens of claim 2, wherein the opposing lateral edges are divergent.

4. The lens of claim 1, wherein at least one plate haptic is approximately between 0.02 and 0.75 mm thick.

5. The lens of claim 1, wherein each of the plate haptics comprises a junction connecting the lens optic to the respective plate haptic.

6. The lens of claim 5, wherein the junction comprises a single flexible hinged strap.

7. The lens of claim 5, wherein the junction comprises a plurality of spaced apart, flexible, hinged straps.

8. The lens of claim 1, wherein each plate haptic comprises acrylic.

9. The lens of claim 1, wherein each plate haptic comprises silicone.

10. The lens of claim 1, wherein the lens optic comprises acrylic.

11. The lens of claim 1, wherein the lens optic comprises silicone.

12. The lens of claim 1, wherein the lens optic and the pair of plate haptics comprise a same material, the same material being acrylic.

13. An intraocular lens comprising:
a lens optic; and
a pair of plate haptics coupled to the lens optic, each of the plate haptics having a proximal edge, a distal edge, and opposing lateral edges extending from the proximal edge to the distal edge, the proximal edge of each plate haptic being closer to the optic than the distal edge;
wherein each plate haptic comprises a pair of appendages at least partially surrounding the optic and entirely displaced from a distal end of said plate haptic, each appendage formed by a portion of one of the lateral edges and a portion of the proximal edge, a proximal end portion of each appendage being spaced apart from the lens optic;

wherein a longitudinal axis of the intraocular lens extends through each of the plate haptics, a transverse diameter of the lens optic being perpendicular to the longitudinal axis of the intraocular lens;

wherein a width is measured between medial edges of the proximal end portions of the appendages of the same haptic, the width being greater than the transverse diameter of the lens optic;

wherein each appendage comprises:
a planar section co-planar and co-extensive with said appendage's respective haptic, the plate appendage comprising a proximal cantilevered extension of said appendage's respective haptic, and each appendage being spaced laterally and radially outwardly from the optic;
a convex end portion; and
a medial edge contoured with respect to the optic;

wherein each haptic and said haptic's associated pair of appendages together only partially surrounding the optic, the appendages being curved;

wherein an angle of extension of one of the appendages from the proximal edge of the haptic is non-convergent with respect to the angle of extension of other appendage of the same haptic;

wherein the pair of appendages extending from each haptic form a maximum transverse dimension of the intraocular lens that is greater than the transverse diameter of the lens optic, a longitudinal dimension of the intraocular lens measured along the longitudinal axis of the intraocular lens being greater than the maximum transverse dimension.

14. The lens of claim 13, wherein each plate haptic comprises acrylic.

15. The lens of claim 13, wherein each plate haptic comprises silicone.

16. The lens of claim 13, wherein the lens optic comprises acrylic.

17. The lens of claim 13, wherein the lens optic comprises silicone.

18. The lens of claim 13, wherein the lens optic and the pair of plate haptics comprise a same material, the same material being acrylic.

* * * * *